United States Patent
Palmer et al.

(10) Patent No.: US 11,602,384 B2
(45) Date of Patent: Mar. 14, 2023

(54) METHODS FOR GENERATING AND APPLYING COMPRESSION WITHIN A BODY

(71) Applicant: Arthrex, Inc., Naples, FL (US)

(72) Inventors: Matthew Palmer, Cambridge, MA (US); Matthew Fonte, Concord, MA (US); Robert Devaney, Auburndale, MA (US); Kaitlyn Nealon, Boston, MA (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 17/872,175

(22) Filed: Jul. 25, 2022

(65) Prior Publication Data
US 2022/0354556 A1    Nov. 10, 2022

Related U.S. Application Data

(60) Continuation of application No. 17/392,566, filed on Aug. 3, 2021, which is a continuation of application No. 16/416,930, filed on May 20, 2019, now Pat. No. 11,103,293, which is a division of application No. 15/288,131, filed on Oct. 7, 2016, now Pat. No. 10,292,745.

(60) Provisional application No. 62/293,453, filed on Feb. 10, 2016, provisional application No. 62/238,199, filed on Oct. 7, 2015, provisional application No. 62/238,210, filed on Oct. 7, 2015.

(51) Int. Cl.
| | |
|---|---|
| *A61B 17/72* | (2006.01) |
| *A61B 17/86* | (2006.01) |
| *A61B 17/88* | (2006.01) |
| *A61B 17/00* | (2006.01) |

(52) U.S. Cl.
CPC ........ *A61B 17/863* (2013.01); *A61B 17/7291* (2013.01); *A61B 17/866* (2013.01); *A61B 17/8685* (2013.01); *A61B 17/8872* (2013.01); *A61B 2017/00867* (2013.01)

(58) Field of Classification Search
CPC .. A61B 17/7216–7225; A61B 17/7291; A61B 17/84–8695
See application file for complete search history.

(56) References Cited

U.S. PATENT DOCUMENTS

| | | | |
|---|---|---|---|
| 6,306,140 B1 * | 10/2001 | Siddiqui | A61B 17/863 606/315 |
| 7,175,626 B2 | 2/2007 | Neff | |
| 7,985,222 B2 | 7/2011 | Gall | |
| 8,080,044 B2 | 12/2011 | Biedermann | |
| 8,864,804 B2 * | 10/2014 | Champagne | A61B 17/869 606/315 |
| 8,998,999 B2 | 4/2015 | Lewis | |
| (Continued) | | | |

FOREIGN PATENT DOCUMENTS

JP    H0910224 A    1/1997

*Primary Examiner* — Eduardo C Robert
*Assistant Examiner* — Steven J Cotroneo
(74) *Attorney, Agent, or Firm* — McDonnell Boehnen Hulbert & Berghoff LLP

(57) ABSTRACT

This disclosure describes exemplary screw and intramedullary devices that are better able to bring bone fragments into close proximity with each other, generate a compressive load, and maintain that compressive load for a prolonged period of time while healing occurs. The devices are made of a shape memory material.

10 Claims, 13 Drawing Sheets

(56) References Cited

U.S. PATENT DOCUMENTS

| | | |
|---|---|---|
| 9,056,014 B2 | 6/2015 | McCormick |
| 9,282,977 B2 | 3/2016 | Penzimer |
| 9,326,804 B2 | 5/2016 | Biedermann |
| 9,480,515 B2 * | 11/2016 | Champagne ........ F16B 25/0057 |
| 9,775,630 B2 | 10/2017 | Leavitt |
| 9,808,296 B2 | 11/2017 | McCormick |
| 9,861,413 B2 * | 1/2018 | Palmer ................. A61B 17/863 |
| 10,383,671 B2 | 8/2019 | Prandi |
| 10,478,238 B2 * | 11/2019 | Palmer ............... A61B 17/7014 |
| 2004/0068261 A1 * | 4/2004 | Fourcault ............ A61B 17/863 606/67 |
| 2004/0230193 A1 * | 11/2004 | Cheung ............. A61B 17/7266 606/63 |
| 2005/0277940 A1 * | 12/2005 | Neff ................... A61B 17/8875 606/310 |
| 2006/0264954 A1 * | 11/2006 | Sweeney, II ....... A61B 17/8685 606/328 |
| 2009/0198287 A1 | 8/2009 | Chiu |
| 2009/0210016 A1 | 8/2009 | Champagne |
| 2009/0264937 A1 | 10/2009 | Parrott |
| 2010/0211115 A1 | 8/2010 | Tyber |
| 2014/0257420 A1 | 9/2014 | Fox |
| 2015/0011998 A1 * | 1/2015 | McCormick ........ A61F 5/05875 606/56 |
| 2015/0141994 A1 | 5/2015 | Cheney |
| 2016/0015438 A1 | 1/2016 | Elleby |
| 2016/0095638 A1 | 4/2016 | Reimels |
| 2017/0360489 A1 | 12/2017 | Palmer |

\* cited by examiner

METHODS FOR GENERATING AND APPLYING COMPRESSION WITHIN A BODY

CROSS-REFERENCE TO RELATED APPLICATION

This application is a continuation of U.S. patent application Ser. No. 17/392,566, filed on Aug. 3, 2021; which is a continuation of U.S. patent application Ser. No. 16/416,930 filed on May 20, 2019, issued as U.S. Pat. No. 11,103,293 on Aug. 31, 2021; which is a divisional application of U.S. patent application Ser. No. 15/288,131, filed on Oct. 7, 2016, issued as U.S. Pat. No. 10,292,745 on May 21, 2019; which claims priority to U.S. Provisional Application No. 62/238,199 filed on Oct. 7, 2015; and claims priority to U.S. Provisional Application No. 62/238,210 filed on Oct. 7, 2015; and claims priority to U.S. Provisional Application No. 62/293,453, which was filed on Feb. 10, 2016. The above-noted Applications are incorporated by reference as if set forth fully herein.

TECHNICAL FIELD

This disclosure relates to devices and methods for generating, applying, and maintaining compression to a site in a human or animal body in order to effect healing of diseased or damaged tissue. The disclosure finds particular utility in the field of orthopedics and specifically for generating and maintaining compression between bone fragments that are to be fused. While the disclosure has application throughout the body, its utility will be described herein in the context of the repair of injured bone tissue, such as the proximal and distal interphalangeal joint of the second, third, or fourth toe and/or fingers. Additionally, the disclosure has application to aid in the fusion of broken ribs, etc.

BACKGROUND

In the field of orthopedic surgery, it is common to rejoin broken bones. The success of the surgical procedure often depends on the successful reapproximation of the bone fragments, the amount of compression achieved between the bone fragments, and the ability to maintain that compression between the bone fragments. If the surgeon is unable to bring the bone fragments into close contact, a gap will exist between the bone fragments and the bone tissue will need to fill that gap before complete healing can take place. Furthermore, gaps between bone fragments that are too large allow motion to occur between the bone fragments, disrupting the healing tissue and thus slowing the healing process. Optimal healing requires that the bone fragments be in close contact with each other, and for a compressive load to be applied and maintained between the bone fragments. Compressive strain between bone fragments has been found to accelerate the healing process in accordance with Wolf s Law.

Broken bones can be rejoined using screws, staples, plates, pins, intramedullary devices, and other devices known in the art. These devices are designed to assist the surgeon with reducing the fracture and creating a compressive load between the bone fragments. Intramedullary devices are often used for fractures of the long bones; however, they are also frequently used in the phalanges and specifically for the treatment of "hammer toe", which is a deformity of the proximal interphalangeal joint of the second, third, or fourth toe causing the toe to be permanently bent. Typical intramedullary devices used in the phalanges have opposing ends that are adapted to grip against the wall of the intramedullary canal. These intramedullary devices are typically made of titanium alloys, stainless steel alloys, Nitinol and other materials, e.g., PEEK. The titanium alloy devices and stainless steel alloy devices often have barbs or threaded regions at their opposing ends to grip the wall of the intramedullary canal. The Nitinol devices typically have a pair of radially extending "legs" at their opposing ends that expand outward when warmed to body temperature, with the pair of legs at each end being disposed in a common plane.

While these intramedullary devices are designed to bring the bone fragments into close contact and to generate a compressive load between the bone fragments, these devices do not always succeed in accomplishing this objective. The compressive load dissipates rapidly as the bone relaxes and remodels. Furthermore, gripping the bone with only a pair of coplanar legs does not provide significant torsional stability to the fusion site.

Thus, there exists a clinical need for intramedullary devices that are better able to bring bone fragments into close proximity with each other, generate a compressive load, and maintain that compressive load for a prolonged period of time while healing occurs.

SUMMARY

This disclosure contemplates the provision and use of a novel screw and intramedullary devices that are better able to bring bone fragments into close proximity with each other, generate compressive loads, and maintain the compressive loads for a prolonged period of time while healing occurs.

In an exemplary embodiment, a compression screw is provided which is manufactured from a shape memory material. The shape memory material may be a metal alloy (e.g., Nitinol) or a polymer (e.g., appropriately processed PEEK). The compression screw is designed to engage bone fragments and to generate compression between the bone fragments. The compression screw has a proximal threaded region and a distal threaded region. The thread pitch on the proximal threaded region is finer than the thread pitch on the distal threaded region (i.e., the thread pitch on the proximal threaded region has more threads per inch than the thread pitch on the distal threaded region). This pitch differential aids in reducing fractures and generating compression between the bone fragments.

The thread geometry on the proximal threaded region and the distal threaded region are mirrored to create a "bookend" effect that increases the compression holding capabilities of the screw (e.g., the thread geometry on the proximal threaded region has an incline in the proximal direction and a flat surface in the distal direction that is substantially perpendicular to the longitudinal axis of the screw, and the thread geometry on the distal threaded region is mirrored, having an incline in the distal direction and a flat surface in the proximal direction that is substantially perpendicular to the longitudinal axis of the screw).

The two threaded regions are connected by a hollow central bridge region. The hollow central bridge region can be strained and reversibly elongated, e.g., up to about 8% where the compression screw is formed from Nitinol. The hollow central bridge region may be strained and reversibly elongated prior to implantation by releasing that strain after implantation of the compression screw across the fracture line. The contracting hollow central bridge region can aid in fracture reduction and provide additional therapeutic compression to the bone fracture to provide superior healing.

Furthermore, the contracting hollow central bridge region can be shape set to have a 10° axial bend. The bend can be reversibly straightened prior to implantation (while also being reversibly elongated), and by releasing that straightening and elongation after implantation of the compression screw across the fracture line, the hollow central bridge region can return to its 10° bend to provide a more anatomical healing and can return to its un-elongated state to aid in fracture reduction and provide additional therapeutic compression to the bone fracture.

It should be appreciated that the reversible elongation does not need to be coupled with the 10° bend. It may be beneficial for the compression screws of this disclosure not to undergo reversible elongation, and instead only return to a state with an axial bend following implantation.

In an exemplary embodiment, a compression screw system includes a compression screw having a shaft, a screw thread formed on the shaft at a distal location, and a bone-engaging feature formed on the shaft at a proximal location. At least a portion of the shaft disposed between the screw thread and the bone-engaging feature is non-linear but is capable of being bent to a linear state, and is further capable of being stretched. A holding element is connectable to the compression screw for releasably holding at least a portion of the shaft in a linear, stretched condition.

In another exemplary embodiment, an apparatus for securing a first bone fragment to a second bone fragment includes a fusion device including a cannulated shaft having a first end and a second end, a first bone-engaging feature formed on the shaft at a first location, and a second bone-engaging feature formed on the shaft at a second location. The first bone-engaging feature includes a thread such that the first end of the shaft may be advanced into a hole in the first bone fragment. The second bone-engaging feature includes at least one barb which, in its unbiased condition, is largely co-radial with the longitudinal axis of the shaft and is capable of being elastically deformed so that the barbs occupy the region of the cannulation of the shaft such that the second end of the shaft may be advanced into a hole in the second bone fragment. The second end is prevented from being withdrawn from the hole in the second bone fragment when the at least one barb is in its unbiased condition.

In yet another exemplary embodiment, a fusion device includes a cannulated shaft having a first end and a second end, a first bone-engaging feature formed on the shaft at a first location, and a second bone-engaging feature formed on the shaft at a second location. The cannulated shaft can be elongated and constrained in a second state, and upon releasing the constraint, the shaft returns to its un-elongated state. The first bone-engaging feature includes a thread such that the first end of the shaft may be advanced into a hole in the first bone fragment. The second bone-engaging feature includes at least one barb which, in its unbiased condition, is largely co-radial with the longitudinal axis of the shaft and is capable of being elastically deformed so that the barbs occupy the region of the cannulation of the shaft. The second end of the shaft may be advanced into a hole in the second bone fragment and is prevented from being withdrawn from the hole in the second bone fragment when the at least one barb is in its unbiased condition.

In yet another exemplary embodiment, an apparatus for securing a first bone fragment to a second bone fragment includes a fusion device having a cannulated shaft having a first end and a second end, a first bone-engaging feature formed on the shaft at a first location, and a second bone-engaging feature formed on the shaft at a second location. The first bone-engaging feature includes a thread such that the first end of the shaft may be advanced into a hole in the first bone fragment. The second bone-engaging feature formed includes a pair of planar barbs that, in their unbiased condition, extend radially from the longitudinal axis of the shaft and are capable of being elastically deformed so that the barbs collapse so as to be largely parallel with the longitudinal axis of the shaft. The second end of the shaft may be advanced into a hole in the second bone fragment and is prevented from being withdrawn from the hole in the second bone fragment when the pair of barbs is in its unbiased condition.

In yet another exemplary embodiment, an apparatus for securing a first bone fragment to a second bone fragment includes a fusion device. The device includes a cannulated shaft having a first end and a second end. The cannulated shaft can be elongated and constrained in a second state, and upon releasing the constraint, the shaft returns to its un-elongated state. A first bone-engaging feature is formed on the shaft at a first location and a second bone-engaging feature is formed on the shaft at a second location. The first bone-engaging feature includes a thread such that the first end of the shaft may be advanced into a hole in the first bone fragment. The second bone-engaging feature includes a pair of planar barbs that, in their unbiased condition, extend radially from the longitudinal axis of the shaft and are capable of being elastically deformed so that the barbs collapse so as to be largely parallel with the longitudinal axis of the shaft. The second end of the shaft may be advanced into a hole in the second bone fragment and is prevented from being withdrawn from the hole in the second bone fragment when the pair of barbs is in its unbiased condition.

BRIEF DESCRIPTION OF THE DRAWINGS

The various features and advantages of this disclosure will become apparent to those skilled in the art from the following detailed description. The drawings that accompany the detailed description can be briefly described as follows.

DETAILED DESCRIPTION

Figure 1:
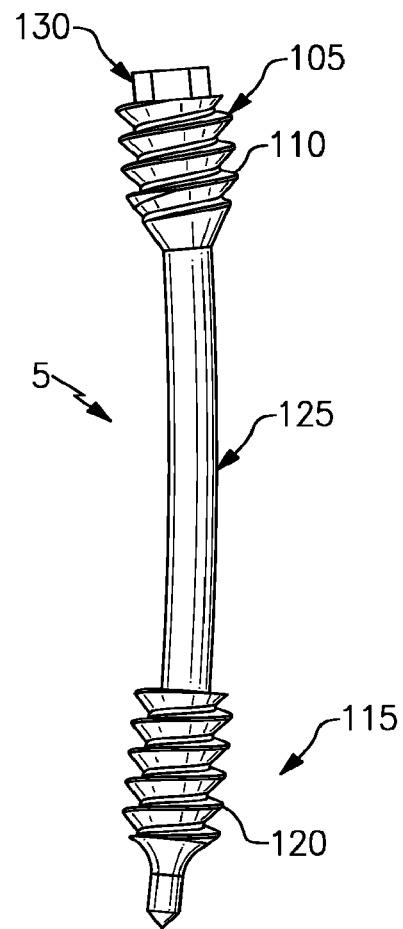
FIGS. 1, 2, 3, and 4 schematically illustrate a compression screw system according to an exemplary aspect of this disclosure.

This disclosure describes the use of novel intramedullary devices that are better able to bring bone fragments into close proximity with each other, generate a compressive load, and maintain that compressive load for a prolonged period of time while healing occurs.

A compression screw system according to an exemplary aspect of this disclosure includes, inter alia, a compression screw and an internal retaining pin. The compression screw is made of a shape memory material such that a portion of a shaft of the compression screw is positionable in a bent condition. The internal retaining pin is insertable into the compression screw and is configured for moving the portion from the bent condition to a straightened and stretched condition.

In a further embodiment, an internal retaining pin holds a portion of a shaft in a straightened and stretched condition while a compression screw is inserted into a bone, and the internal retaining pin is configured for releasing the portion from the stretched and straightened condition back toward a bent condition after the compression screw has been inserted into the bone.

In a further embodiment, a shape memory material is Nitinol.

In a further embodiment, a shape memory material is PEEK.

In a further embodiment, a compression screw includes a central lumen, and an internal retaining pin extends into the central lumen.

In a further embodiment, an internal retaining pin is seated against an annular shoulder of a central lumen when a portion of a shaft is in a straightened and stretched condition.

In a further embodiment, a first screw thread is formed on a shaft at a distal location and a second screw thread is formed on the shaft at a proximal location, and a portion of the shaft is disposed between the first and second screw threads.

In a further embodiment, a first screw thread and a second screw thread include different thread pitches.

In a further embodiment, a portion of a compression screw is bent at an angle of about 10° relative to a longitudinal axis of the compression screw when in a bent condition.

In a further embodiment, a first drive feature is provided on a compression screw and a second drive feature is provided on an internal retaining pin, and the first drive feature and the second drive feature are engageable to insert the compression screw into bone.

An intramedullary fusion device according to an exemplary aspect of this disclosure includes, inter alia, a shaft made of a shape memory material and including a threaded end region, a barbed end region, and a central bridge region between the threaded end region and the barbed end region. A first bone-engaging feature is provided on the threaded end region, and a second bone-engaging feature is provided on the barbed end region. The second bone-engaging feature is movable between an unbiased condition in which it is co-radial with a longitudinal axis of the shaft and a biased condition in which a cross-sectional profile of the barbed end region is reduced.

In a further embodiment, a shape memory material is Nitinol.

In a further embodiment, a shape memory material is PEEK.

In a further embodiment, a first bone-engaging feature includes a thread helically wrapped around a shaft at a threaded end region.

In a further embodiment, a second bone-engaging feature includes a pair of planar barbs.

In a further embodiment, a pair of planar barbs are generally parallel to the longitudinal axis of the shaft when positioned in the biased condition.

In a further embodiment, a second bone-engaging feature occupies at least a portion of a cannulation that extends through a shaft when a second bone-engaging feature is positioned in a biased condition.

In a further embodiment, a central bridge region is neither threaded nor barbed.

In a further embodiment, an intramedullary fusion device is receivable within a recess of a delivery device.

In a further embodiment, a second bone-engaging feature is removably held within a recess of a delivery device.

FIGS. 1-4 illustrate a compression screw 5 for bringing bone fragments into close proximity with each other, generating a compressive load, and maintaining that compressive load for a prolonged period of time while the bone tissue heals. The compression screw 5 is manufactured from a shape memory material (e.g., a material capable of exhibiting superelasticity and/or a temperature induced shape change). The shape memory material may be a metal alloy (e.g., Nitinol) or a polymer (e.g., appropriately processed PEEK). The compression screw 5 is designed to engage bone fragments and generate compression between the bone fragments.

The compression screw 5 includes a proximal threaded region 105 having a proximal screw thread 110 and a distal threaded region 115 having a distal screw thread 120. The thread pitch of proximal screw thread 110 is finer than the thread pitch of distal screw thread 120 (i.e., the thread pitch on proximal threaded region 105 has more threads per inch than the thread pitch on distal threaded region 115). This pitch differential reduces fractures and generates compression. The respective thread geometry on the proximal threaded region 105 and the distal threaded region 115 are mirrored, thus creating a "book-end" effect that increases the compression holding capabilities of the compression screw 5 when it extends across a fracture line in bone (e.g., the thread geometry on the proximal threaded region 105 has an incline in the proximal direction and a flat surface in the distal direction that is substantially perpendicular to the longitudinal axis of the screw, and the thread geometry on the distal threaded region 115 is mirrored, having an incline in the distal direction and a flat surface in the proximal direction that is substantially perpendicular to the longitudinal axis of the screw).

The proximal threaded region 105 and the distal threaded region 115 are connected by a hollow central bridge region 125. The hollow central bridge region 125 can be strained and reversibly elongated because the compression screw 5 is manufactured from a shape memory material. In an embodiment, the compression screw 5 is formed out of Nitinol, and the hollow central bridge region 125 can be strained and reversibly elongated by up to 8% without taking a set. By straining and reversibly elongating the hollow central bridge region 125 prior to implantation across a bone fracture line, and by thereafter releasing that strain after implantation across the fracture line, the hollow central bridge region 125 can provide additional compression to the bone fracture.

The compression screw 5 includes a drive feature 130 (e.g., a hexagonal boss) at the proximal threaded region 105 for engagement by an appropriate driver (not shown) for turning the compression screw 5 (e.g., into bone). Additionally, the distal threaded region 115 of the compression screw 5 may include self-drilling features (e.g., cutting edges) and self-tapping features (e.g., flutes), although not specifically shown in the figures.

The compression screw 5 also includes a central lumen 145 (see FIG. 4) which extends the length of the proximal threaded region 105 and the central bridge region 125. The central lumen 145 generally includes a distal bore 150 and a proximal counterbore 160. The distal bore 150 terminates at an annular shoulder 165 that may lie in a plane perpendicular to the longitudinal axis of the compression screw 5.

The proximal counterbore 160 has a diameter which is wider than the diameter of the distal bore 150. The proximal counterbore 160 is threaded, e.g., with an internal thread 175 (for purposes of clarity, not shown).

Figure 2:
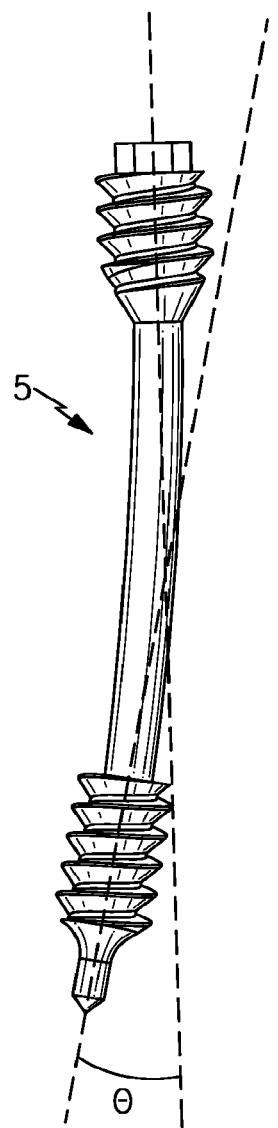
Figure 3:
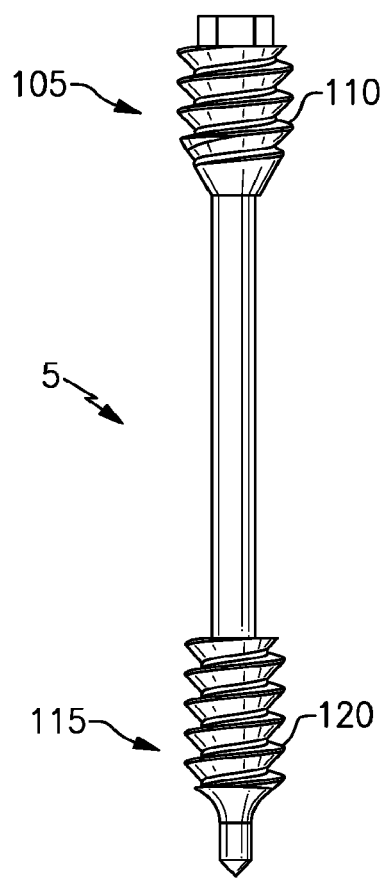
Figure 4:
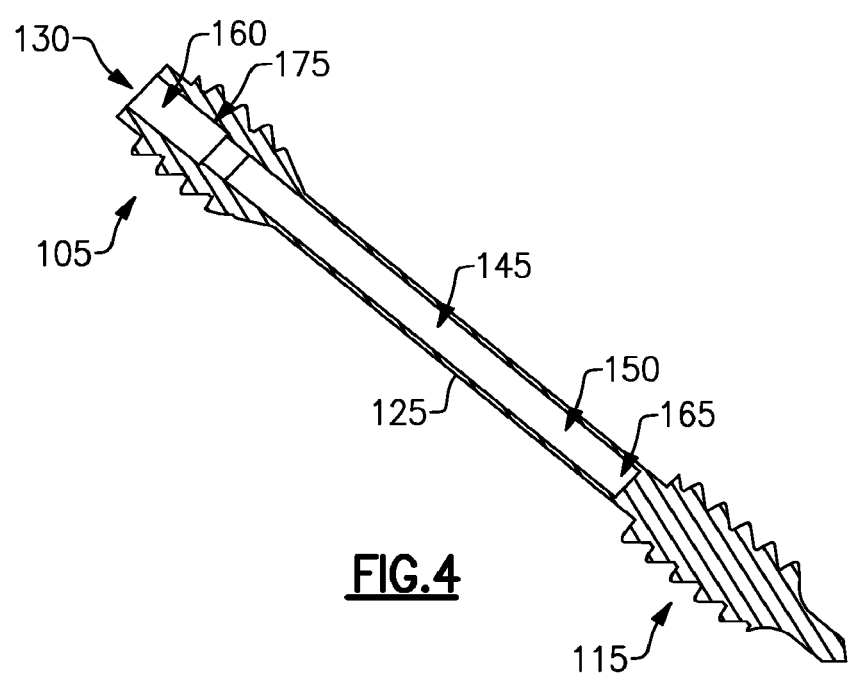

In the un-constrained state, the central bridge region 125 may be bent along its central axis. In an embodiment, such as shown in FIG. 2, the hollow central bridge region 125 may be bent at an angle Θ (e.g., up to about 10°) relative to the central axis.

Figure 5:
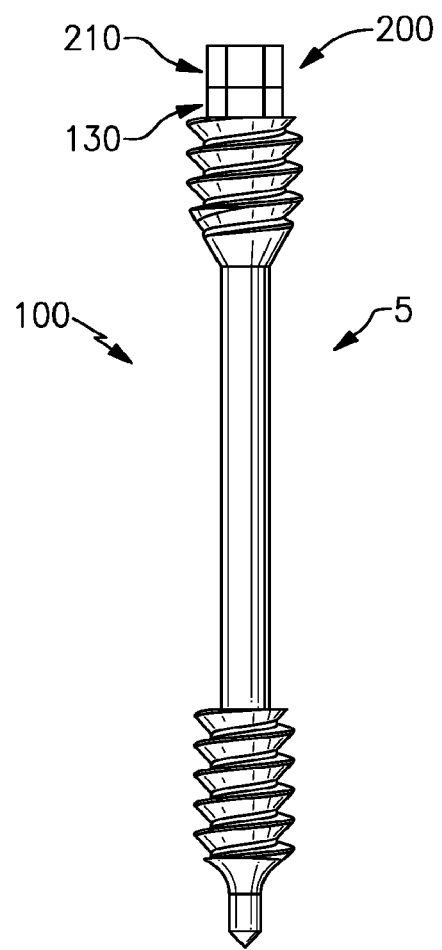
FIGS. 5 and 6 schematically illustrate internal retaining points disposed within the interior of a strained (i.e., stretched) and straightened (i.e., un-bent) compression screw.
Figure 6:
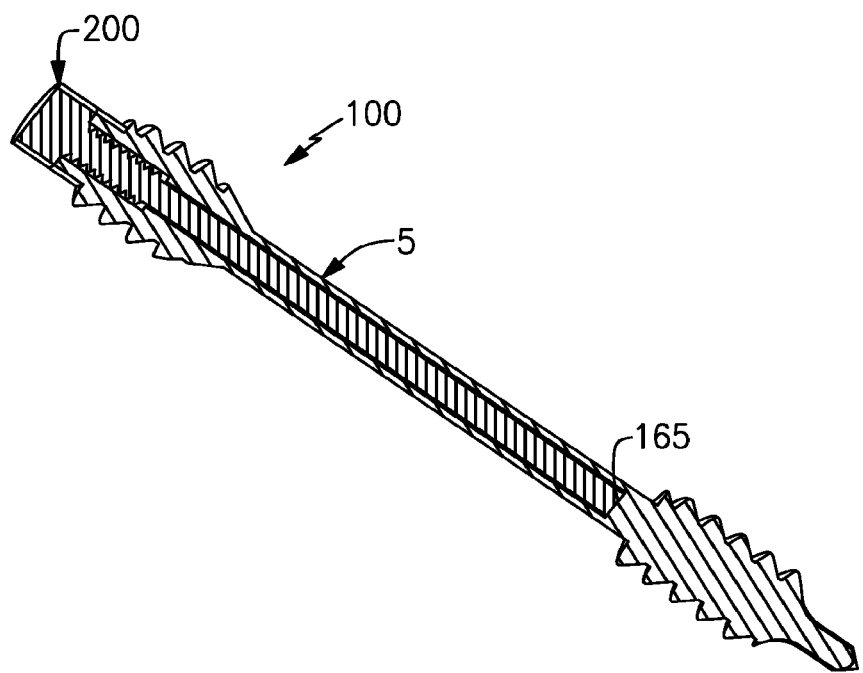

FIGS. 5-6 illustrate a compression screw system 100. The compression screw system 100 generally includes a compression screw 5 and an internal retaining pin 200. In an embodiment, the compression screw 5 and the internal retaining pin 200 are provided as part of a sterilized kit. The kit may include additional instruments to aid in the implantation of the compression screw 5 (e.g., k-wire, drill bit, screw size guide, etc.).

The internal retaining pin 200 is selectively inserted into the compression screw 5. The internal retaining pin 200 is sized so that when the compression screw 5 is strained (i.e., stretched) and un-bent (i.e., straightened), the internal retaining pin 200 is fully seated against the annular shoulder 165 of the distal bore 150 of the central lumen 145 (see FIG. 6).

The internal retaining pin 200 is capable of maintaining the compression screw 5 strained and straightened. The compression screw system 100 is implanted by driving the compression screw 5 using a drive feature 210 of the internal retaining pin 200 and the drive feature 130 of the compression screw 5. Upon implantation, removal of the internal retaining pin 200 causes the compression screw 5 to attempt to shorten to its original length and also bend to its bent state.

Figure 7:
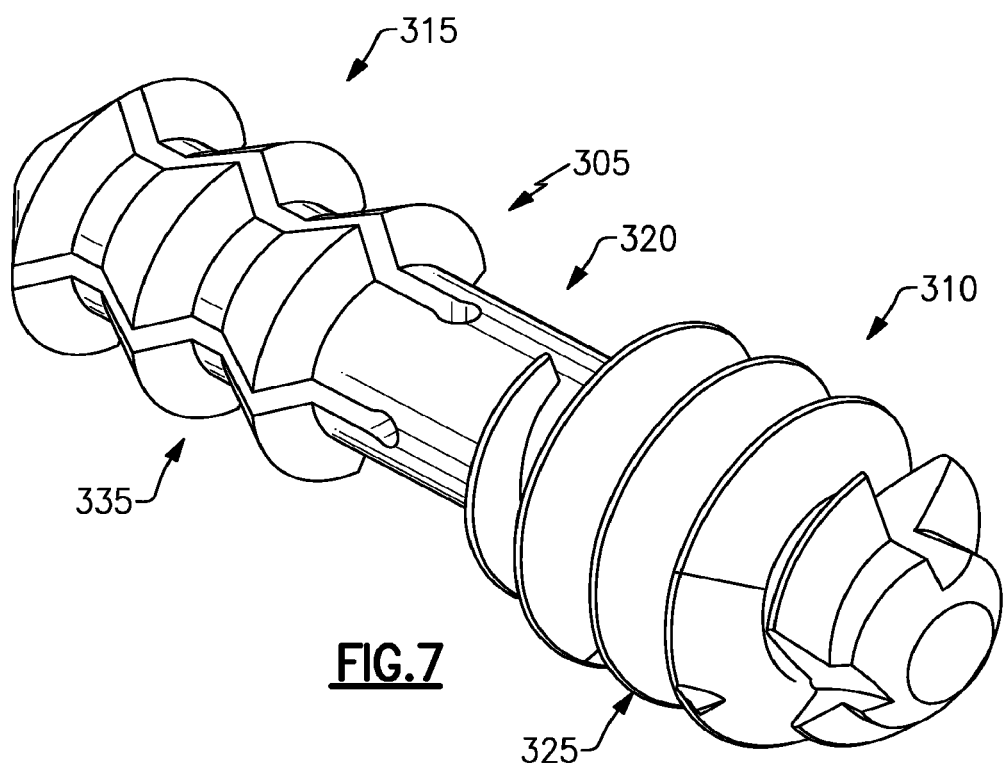
FIGS. 7, 8, and 9 schematically illustrate an intramedullary fusion device according to an exemplary aspect of this disclosure.
Figure 8:
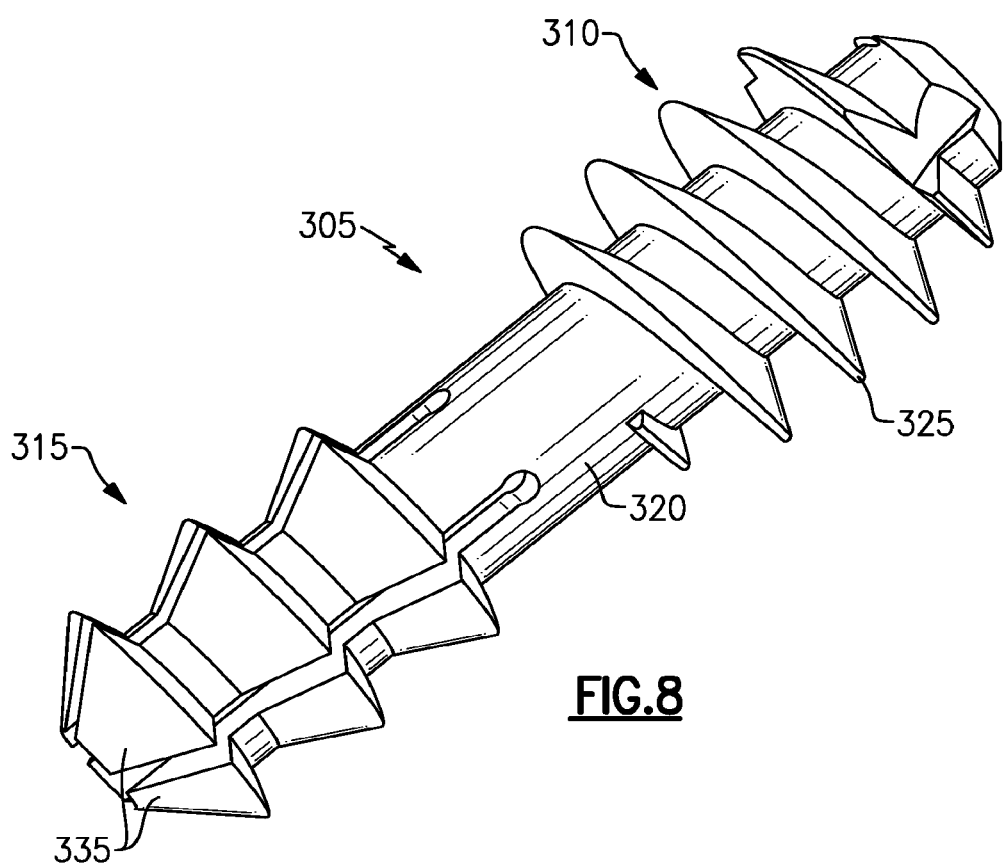
Figure 9:
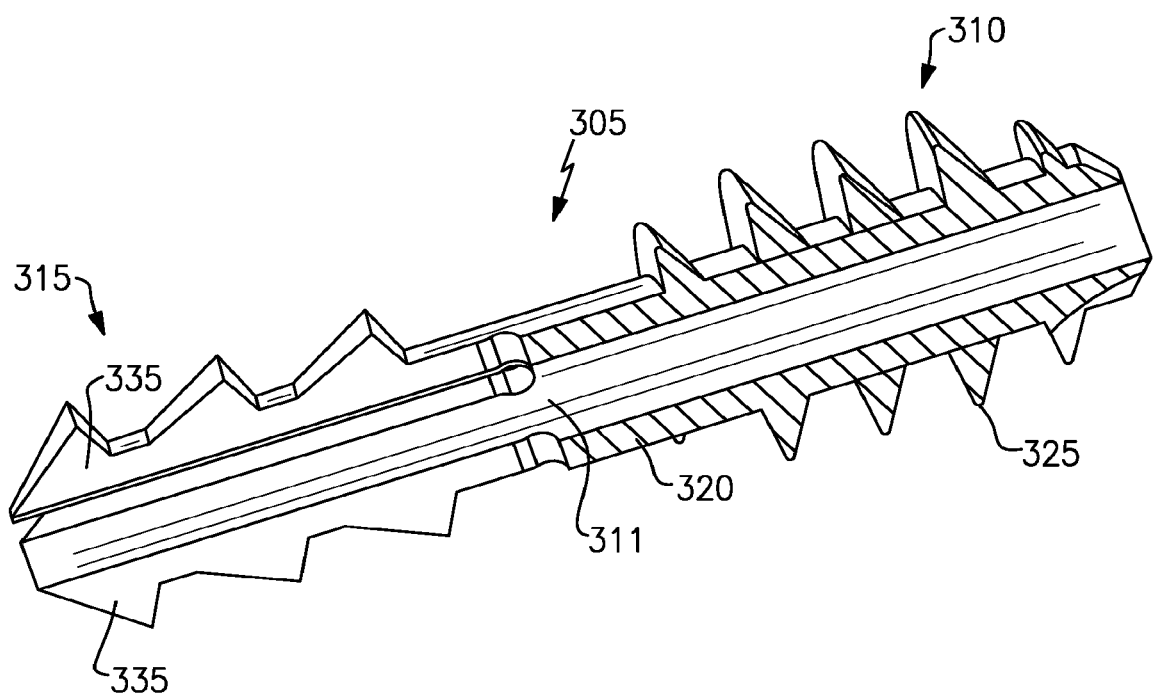

FIGS. 7-9 illustrate an intramedullary fusion device 305 manufactured from a shape memory material. The shape memory material may be a metal alloy (e.g., Nitinol) or a polymer (e.g., appropriately processed PEEK). The intramedullary fusion device 305 includes a threaded end region 310, a barbed end region 315, and a central bridge region 320 connecting the threaded end region 310 to the barbed end region 315. The intramedullary fusion device 305 may be cannulated (see bore or cannulation 311 of FIG. 9) to allow the intramedullary fusion device 305 to be installed over a k-wire if desired, while also allowing a k-wire to be passed through the intramedullary fusion device 305 following implantation if the surgeon desires to fuse a distal or proximal joint. The barbed end region 315 can be reversibly deformed into the cannulation 311 during insertion, and then attempt to return to the un-deformed state following insertion, thereby providing excellent torsional stability at the fusion site.

The threaded end region 310 includes a thread 325 which may be helically wound around the longitudinal axis of the intramedullary fusion device 305. The threaded end region 310 engages the intramedullary canal and distributes pressure across the intramedullary canal post-implantation.

The barbed end region 315 includes a plurality of barbs 335 which, in their unbiased condition, are co-radial with the longitudinal axis of the intramedullary fusion device 305. During implantation, the barbs 335 can be deformed to a position in which they occupy the region of the cannulation 311 so as to reduce the cross-sectional profile of the barbed end region 315. This simplifies insertion into a drilled hole in bone, for example. The barbs 335 can be deformed during implantation in such a way that they partially occupy the cannulation 311 of the intramedullary fusion device 305 (i.e., where barbs 335 are deformed to a point past parallel to the longitudinal axis of intramedullary fusion device 305), thereby further reducing the cross-sectional area of the barbed end region 315. This is beneficial for accessing the intramedullary canal through a small drilled hole, for example.

While FIG. 7 illustrates a device with four barbs 335 on the barbed end region 315, it should be appreciated that barbed end region 315 could include more or fewer barbs. Upon the barbed end region 315 being pressed into a drilled hole, the barbs 335 attempt to return to being co-radial with the body of the intramedullary implant, thus exerting an expansive force on the intramedullary canal.

The central bridge region 320 may include a generally cylindrical shape and may be sized to include an outer diameter that is smaller than the major diameters of the threaded end region 310 and the barbed end region 315.

Figure 10:
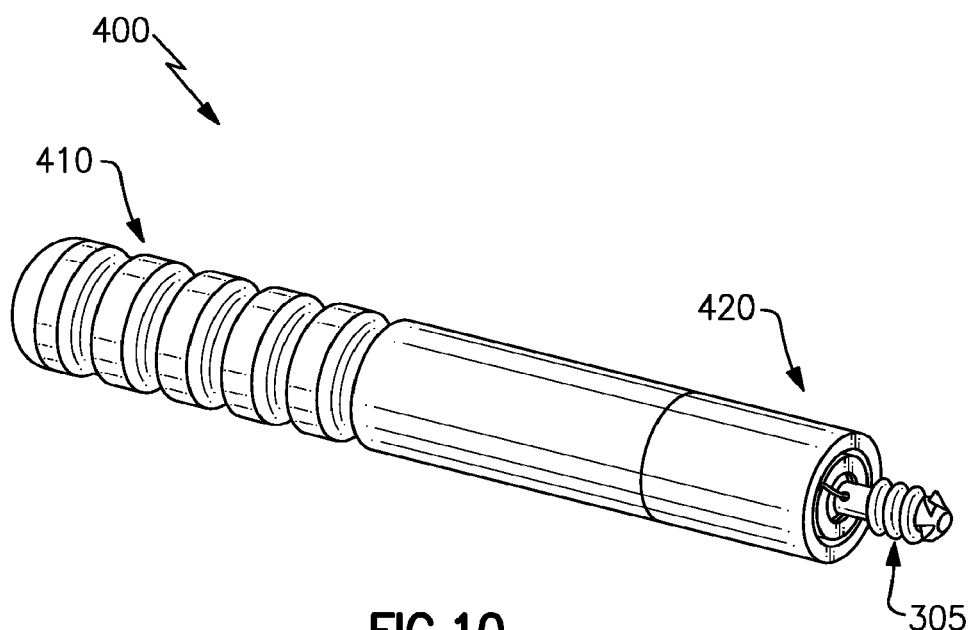
FIGS. 10 and 11 schematically illustrate an intramedullary fusion device loaded onto a delivery device.
Figure 11:
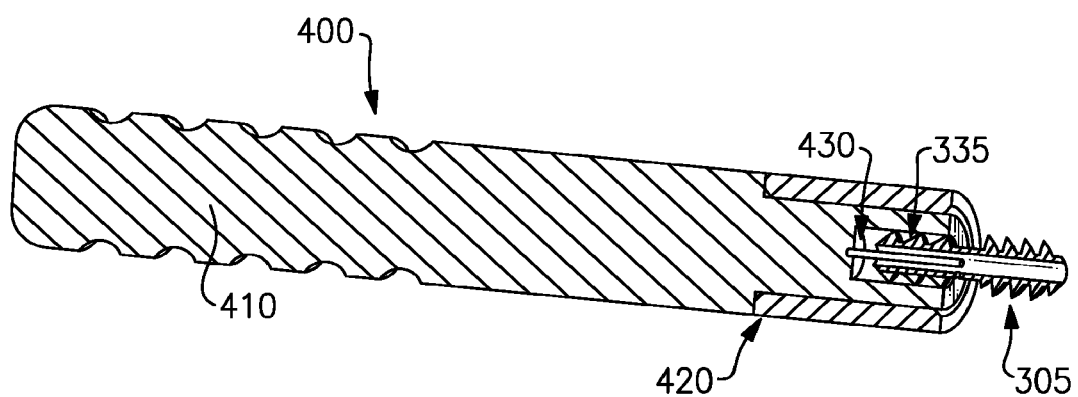

FIGS. 10-11 depict a delivery device 400 for implanting the intramedullary fusion device 305 of FIGS. 7-9. The delivery device 400 includes a handle 410 and an intramedullary engagement region 420. The intramedullary engagement region 420 has one or more drive features 430 that can be positioned between the barbs 335 of the intramedullary fusion device 305. This allows the intramedullary fusion device 305 to be placed in the delivery device 400 and then be screwed into bone. In an embodiment, the intramedullary fusion device 305 is implanted according to the following exemplary method:

1. Perform incisions and bone resections and address soft tissue contractures as necessary. Note: Resections should be perpendicular to the long axis of the bones in the transverse plane. In the sagittal plane, resections should be perpendicular to the long plane.

2. Determine the correct implant size by using a sizing guide.

3. Open the chosen implant kit.

4. Insert a trocar tip of a guide wire into the proximal phalanx along its central axis.

Advance the wire until it pierces the proximal cortex of the proximal phalanx.

5. Place the provided drill bit over the guide wire and drill the proximal phalanx until the boss of the bit meets the cut surface.

6. Remove the drill bit and guide wire.

7. Insert the trocar tip of the guide wire into the middle phalanx along its central axis. Continue to drive the guide wire distally through both middle and distal phalanges until it exists the toe. Continue to drive the guide wire distally until the laser etched line on guide wire contacts the cut surface of the middle phalanx.

8. Using the implant pre-loaded on the delivery device, place the implant/delivery device over the guide wire and drive the threaded portion of the implant into the middle phalanx by screwing it in place. Continue to drive the threaded portion until the rim of the driver is completely flush with the cut surface.

9. Remove and dispose of the driver socket from the implant leaving the barbed portion exposed.

10. Position the implant in line with the proximal phalanx. Insert the barbed portion of the implant into the pre-drilled hole in the proximal phalanx. Apply axial force until the implant is completely buried and the opposing faces of the middle and proximal phalanges come into contact. Optional: If temporary guide wire fixation of the MTP joint is desired, drive the exposed tip of the guide wire through the implant and back into the metatarsal to stabilize the MTP joint.

11. Close the surgical site according to surgical preference. If the guide wire is temporarily left in place, trim with wire cutters.

12. Repeat steps 1-9 for each additional implant used.

Figure 12:
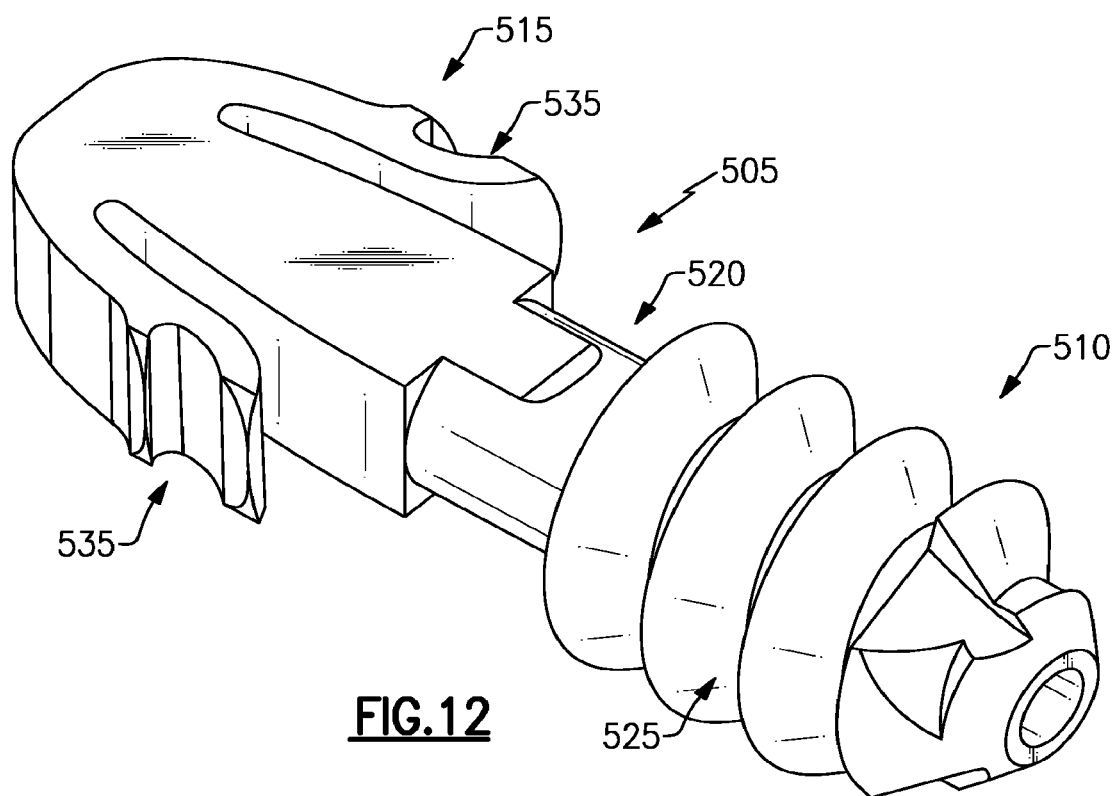
FIGS. 12, 13, and 14 schematically illustrate another exemplary intramedullary fusion device.
Figure 13:
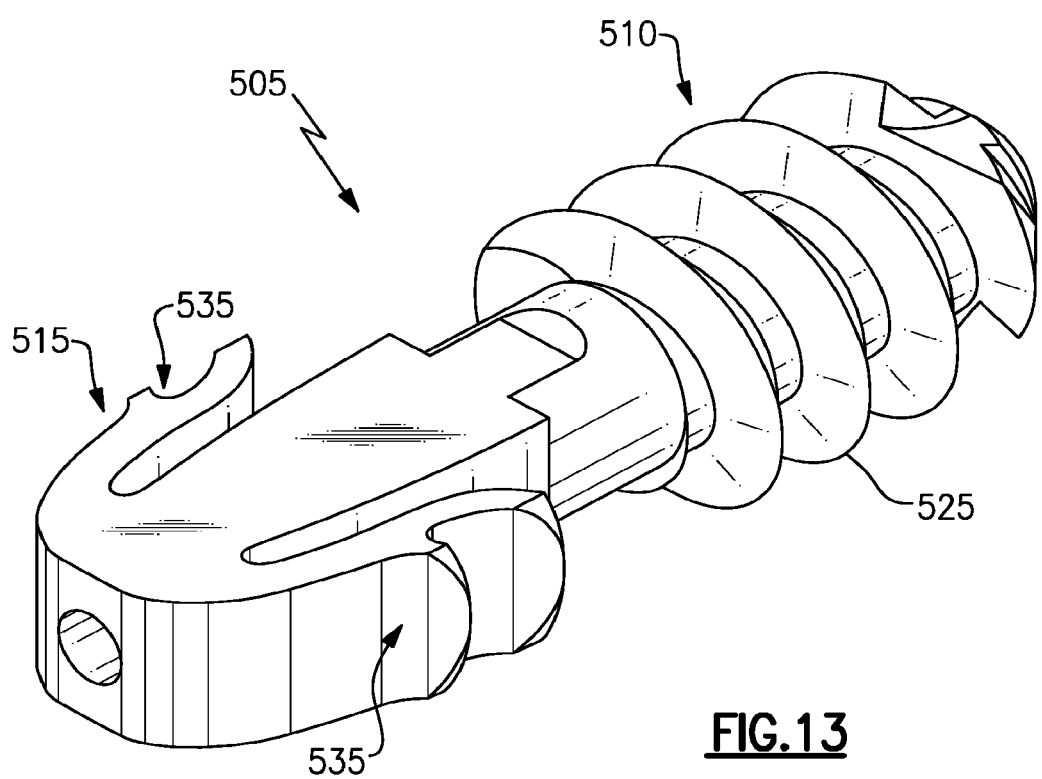
Figure 14:
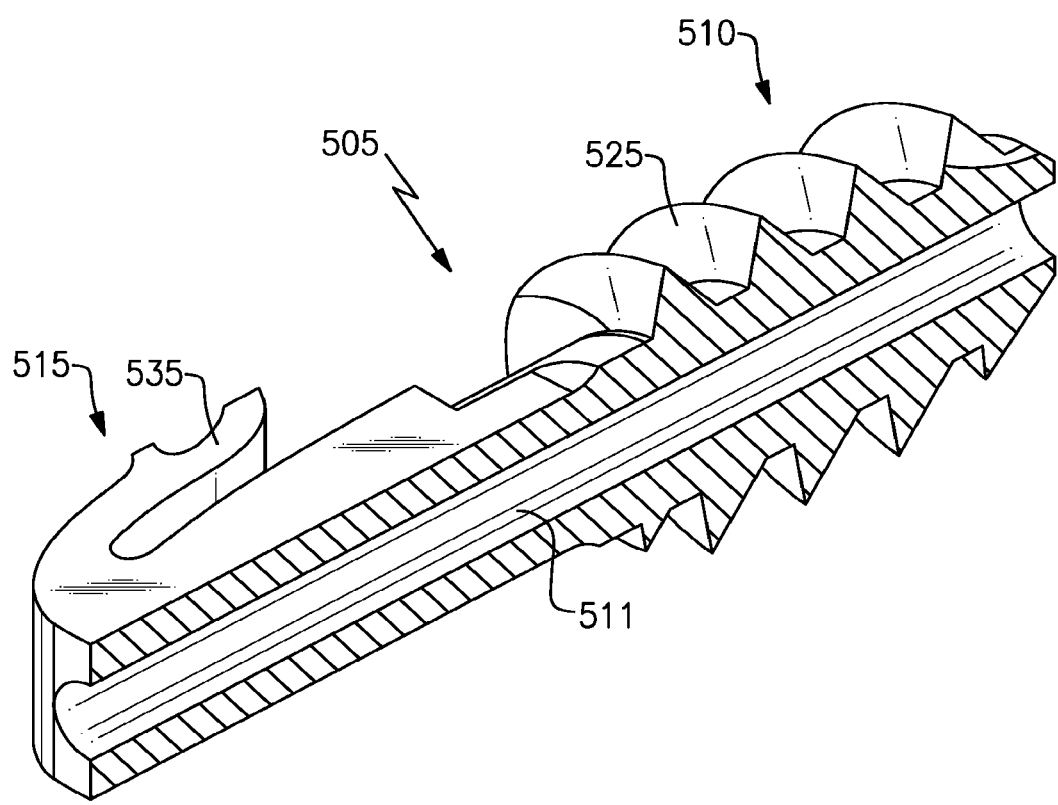

FIGS. 12-14 illustrate another exemplary intramedullary fusion device 505 manufactured from a shape memory material. The shape memory material may be a metal alloy (e.g., Nitinol) or a polymer (e.g., appropriately processed PEEK). The intramedullary fusion device 505 includes a threaded end region 510, a barbed end region 515, and a central bridge region 520 connecting between the threaded end region 510 and the barbed end region 515. The intramedullary fusion device 505 may be cannulated (see bore or cannulation 511 of FIG. 14) to allow the intramedullary fusion device 505 to be installed over a k-wire, or to allow a k-wire to be passed through the intramedullary fusion device 505 following implantation if the surgeon desires to fuse a distal or proximal joint. The barbed end region 515 can reversibly deform such that the barbs are generally parallel to the longitudinal axis of the intramedullary fusion device 505 during insertion, and then attempt to return to the un-deformed state following implantation, thereby providing excellent torsional stability at the fusion site.

The threaded end region 510 includes a thread 525 which is helically wound around the longitudinal axis of the intramedullary fusion device 505. The thread 525 may be self-cutting and/or self-tapping to aid in implantation.

The barbed end region 515 includes a pair of planar barbs 535 which, in their unbiased condition, extend radially from the longitudinal axis of the intramedullary fusion device 505. During implantation, the barbs 535 can be deformed to a position such that they are substantially parallel to the longitudinal axis of the intramedullary fusion device 505 so as to reduce the cross-sectional profile of the barbed end region 515, and thus allowing for insertion into a drilled hole in bone, for example. This is beneficial for accessing the intramedullary canal through a small prepared hole.

While FIG. 12 illustrates a device with a single pair of planar barbs 535 on the barbed end region 515, it should be appreciated that barbed end region 515 can be made with more than one pair of barbs. Upon barbed end region 515 being pressed into a prepared hole, barbs 535 attempt to return to their unbiased configuration and exert an expansive force on the intramedullary canal.

The central bridge region 520 may include a generally cylindrical shape and may be sized to include an outer diameter that is smaller than the major diameters of the threaded end region 510 and the barbed end region 515.

Figure 15:
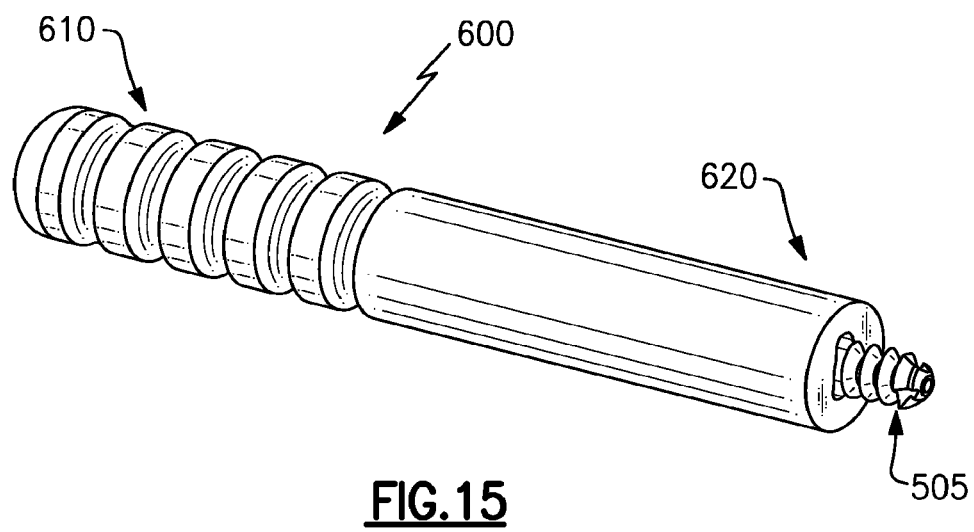
FIGS. 15 and 16 schematically illustrate another intramedullary fusion device loaded onto a delivery device.
Figure 16:
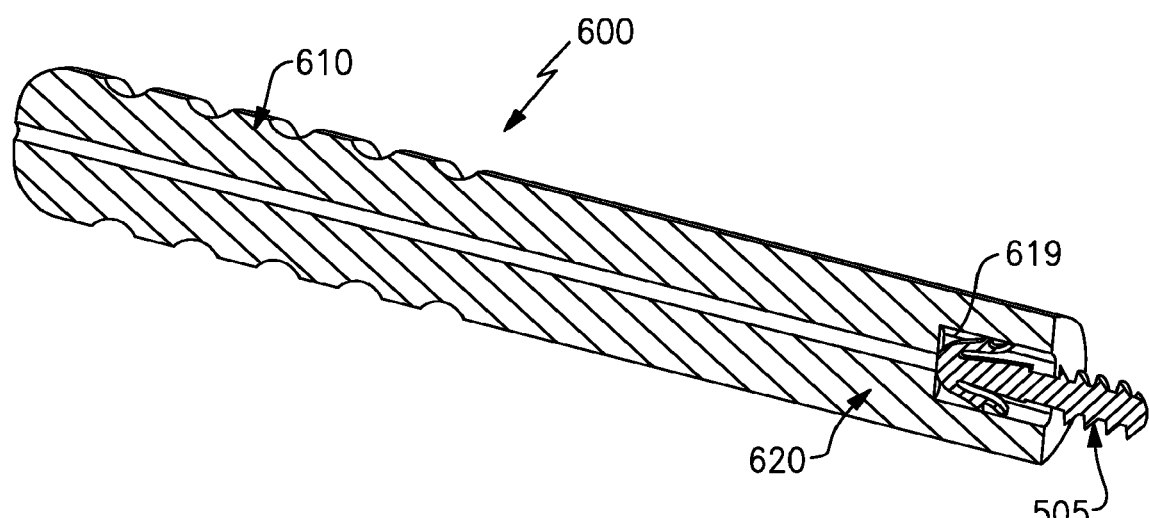

FIGS. 15-16 depict a delivery device 600 for implanting the intramedullary fusion device 505 described above with reference to FIGS. 12-14. The delivery device 600 includes a handle 610 and an intramedullary engagement region 620. The intramedullary engagement region 620 has a recess 619 (see FIG. 16) to accept and hold the intramedullary fusion device 505. This allows the intramedullary fusion device 505 to be placed in the delivery device 600 and then be screwed into the bone. In an embodiment, the intramedullary fusion device 505 is implanted according to the following exemplary method:

1. Perform incisions and bone resections and address soft tissue contractures as necessary. Note: Resections should be perpendicular to the long axis of the bones in the transverse plane. In the sagittal plane, resections should be perpendicular to the long plane.

2. Determine the correct implant size by using a sizing guide.

3. Open the chosen implant kit.

4. Insert a trocar tip of the k-wire into the proximal phalanx along its central axis. Advance the wire until it pierces the proximal cortex of the proximal phalanx.

5. Place the provided drill bit over the guide wire and drill the proximal phalanx until the boss of the bit meets the cut surface.

6. Remove the drill bit and guide wire.

7. Using a supplied broach, broach the drilled hole.

8. Insert a trocar tip of the guide wire into the middle phalanx along its central axis. Continue to drive the guide wire distally through both middle and distal phalanges until it exists the toe. Continue to drive the guide wire distally until the laser etched line on guide wire contacts the cut surface of the middle phalanx.

9. Using the implant pre-loaded on the delivery device, place the implant/delivery device over the guide wire and drive the threaded portion of the implant into the middle phalanx by screwing it in place. Continue to drive the threaded portion until the rim of the driver is completely flush with the cut surface and the implantation driver marking is pointed up.

10. Remove and dispose of the driver socket from the implant leaving the barbed portion exposed.

11. Position the implant in line with the proximal phalanx. Insert the barbed portion of the implant into the prepared hole in the proximal phalanx. Apply axial force until the implant is completely buried and the opposing faces of the middle and proximal phalanges come into contact. Optional: if temporary guide wire fixation of the MTP joint is desired, drive the exposed tip of the guide wire through the implant and back into the metatarsal to stabilize the MTP joint.

12. Close the surgical site according to surgical preference. If the guide wire is temporarily left in place, trim with wire cutters.

13. Repeat steps 1-9 for each additional implant used.

The foregoing description shall be interpreted as illustrative and not in any limiting sense. A worker of ordinary skill in the art would recognize that certain modifications could come within the scope of this disclosure. For these reasons, the following claims should be studied to determine the true scope and content of this disclosure.

What is claimed is:

1. A method for applying compression within a body, the method comprising:
    drilling a hole across a bone fracture line of a patient, wherein the bone fracture line separates a first bone fragment from a second bone fragment;
    positioning a k-wire through the hole;
    positioning the k-wire through a through-hole of a compression implant such that the compression implant is positioned at least partially through the hole, wherein the compression implant includes a shaft having a threaded first end and a second end opposite the threaded first end, wherein the shaft further includes a Nitinol expandable section positioned between the threaded first end and the second end, and wherein the through-hole of the compression implant extends from the threaded first end of the shaft to the second end of the shaft;
    securing the threaded first end of the shaft of the compression implant to the second bone fragment; and
    transitioning, as a driver turns the compression implant, the Nitinol expandable section of the shaft from a first length to a second length, wherein the second length measured along a longitudinal axis of the expandable section is greater than the first length measured along the longitudinal axis of the expandable section, and wherein the Nitinol expandable section is biased to the first length due to the shape memory properties of the Nitinol material to thereby provide a compressive force across the bone fracture line of the patient.

2. A method for applying compression within a body, the method comprising:
- drilling a hole across a bone fracture line of a patient, wherein the bone fracture line separates a first bone fragment from a second bone fragment;
- positioning a compression implant at least partially through the hole, wherein the compression implant includes a shaft having a threaded first end and a second end opposite the threaded first end, and wherein the shaft further includes a Nitinol expandable section positioned between the threaded first end and the second end;
- securing the threaded first end of the shaft of the compression implant to the second bone fragment;
- transitioning, as a driver turns the compression implant, the Nitinol expandable section of the shaft from a first length to a second length, wherein the second length measured along a longitudinal axis of the expandable section is greater than the first length measured along the longitudinal axis of the expandable section, and wherein the Nitinol expandable section is biased to the first length due to the shape memory properties of the Nitinol material to thereby provide a compressive force across the bone fracture line of the patient;
- positioning a k-wire through a through-hole of the compression implant after securing the threaded first end of the shaft of the compression implant to the second bone fragment, wherein the through-hole of the compression implant extends from the threaded first end of the shaft to the second end of the shaft; and
- fusing a joint distal to the bone fracture line.

3. A method for applying compression within a body, the method comprising:
- drilling a hole across a bone fracture line of a patient, wherein the bone fracture line separates a first bone fragment from a second bone fragment;
- positioning a compression implant at least partially through the hole, wherein the compression implant includes a shaft having a threaded first end and a second end opposite the threaded first end, and wherein the shaft further includes a Nitinol expandable section positioned between the threaded first end and the second end;
- securing the threaded first end of the shaft of the compression implant to the second bone fragment; and
- transitioning, as a driver turns the compression implant, the Nitinol expandable section of the shaft from a first length to a second length, wherein the second length measured along a longitudinal axis of the expandable section is greater than the first length measured along the longitudinal axis of the expandable section, and wherein the Nitinol expandable section is biased to the first length due to the shape memory properties of the Nitinol material to thereby provide a compressive force across the bone fracture line of the patient.

4. The method of claim 3, further comprising:
positioning a k-wire through the hole; and
positioning the k-wire through a through-hole of the compression implant prior to securing the threaded first end of the shaft of the compression implant to the second bone fragment, wherein the through-hole of the compression implant extends from the threaded first end of the shaft to the second end of the shaft.

5. The method of claim 3, further comprising:
positioning a k-wire through a through-hole of the compression implant after securing the threaded first end of the shaft of the compression implant to the second bone fragment, wherein the through-hole of the compression implant extends from the threaded first end of the shaft to the second end of the shaft; and
fusing a joint distal to the bone fracture line.

6. The method of claim 3, further comprising:
positioning a k-wire through a through-hole of the compression implant after securing the threaded first end of the shaft of the compression implant to the second bone fragment, wherein the through-hole of the compression implant extends from the threaded first end of the shaft to the second end of the shaft; and
fusing a joint proximal to the bone fracture line.

7. The method of claim 3, wherein the first end of the shaft comprises a self-drilling feature, and wherein the first end of the shaft comprises a self-tapping feature.

8. The method of claim 7, wherein the self-drilling feature comprises one or more cutting edges.

9. The method of claim 7, wherein the self-tapping feature comprises a flute.

10. The method of claim 3, wherein the second length of the expandable section of the shaft is up to 8% greater than the first length of the expandable section of the shaft.

* * * * *